(12) United States Patent
McClurg

(10) Patent No.: US 9,375,301 B2
(45) Date of Patent: Jun. 28, 2016

(54) ARTIFICIAL URINARY SPHINCTER HAVING A MULTI-COMPARTMENT CUFF

(71) Applicant: Coloplast A/S, Humlebaek (DK)

(72) Inventor: Steven McClurg, Brooklyn Park, MN (US)

(73) Assignee: Coloplast A/S, Humlebaek (DK)

( * ) Notice: Subject to any disclaimer, the term of this patent is extended or adjusted under 35 U.S.C. 154(b) by 59 days.

(21) Appl. No.: 13/911,091

(22) Filed: Jun. 6, 2013

(65) Prior Publication Data

US 2014/0364686 A1    Dec. 11, 2014

(51) Int. Cl.
*A61F 2/00* (2006.01)

(52) U.S. Cl.
CPC ..................... *A61F 2/004* (2013.01)

(58) Field of Classification Search
CPC ..... A61F 2/004; A61F 2/0004; A61F 2/0009;
A61F 2/0013; A61F 2/0031; A61F 5/005;
A61F 5/0053; A61F 5/0056; A61F 5/0059;
A61F 5/0063; A61F 2/00; A61F 2/0045;
A61F 2/0063; A61F 2250/0031; A61F
2250/0051; A61F 2/82; A61F 2002/4495;
A61F 2/441; A61F 2250/0012; A61F
2250/0048; A61F 2/02; A61B 2017/00805
USPC ...................................... 600/29–31
See application file for complete search history.

(56) References Cited

U.S. PATENT DOCUMENTS

| | | | |
|---|---|---|---|
| 3,744,063 A | 7/1973 | McWhorter et al. | |
| 4,063,548 A | 12/1977 | Klatt et al. | |
| 4,191,196 A | 3/1980 | Bradley et al. | |
| 4,222,377 A | 9/1980 | Burton | |
| 4,412,530 A | 11/1983 | Burton | |
| 4,878,889 A | 11/1989 | Polyak | |
| 4,909,785 A | 3/1990 | Burton et al. | |
| 4,932,956 A | 6/1990 | Reddy et al. | |
| 4,932,958 A | 6/1990 | Reddy et al. | |
| 4,982,731 A * | 1/1991 | Lue ......................... | A61F 2/26 600/40 |
| 4,994,020 A | 2/1991 | Polyak | |
| 5,078,720 A | 1/1992 | Burton et al. | |
| 5,335,669 A | 8/1994 | Tihon et al. | |
| 5,356,423 A | 10/1994 | Tihon et al. | |

(Continued)

FOREIGN PATENT DOCUMENTS

| | | |
|---|---|---|
| DE | 10023634 A1 | 10/2002 |
| EP | 0093507 | 11/1983 |

(Continued)

OTHER PUBLICATIONS

American Medical Systems, AMS 800TM Urinary Control System Operating Room Manual, 2004.

*Primary Examiner* — Christine H Matthews
(74) *Attorney, Agent, or Firm* — Coloplast Corp., Coloplast A/S; Nick Baumann

(57) ABSTRACT

An artificial urinary sphincter (AUS) system includes a cuff, a pump, and a conduit attachable between the cuff and the pump. The cuff is integrated to include a first compartment and a storage compartment. The first compartment is configured to contact the urethra and the storage compartment communicates with the first compartment. The pump is operable to move the liquid between the first compartment and the storage compartment. The cuff is a pressurizable reservoir that is sized to be placed around a urethra of a user and configured to coapt the urethra in treating urinary incontinence.

3 Claims, 8 Drawing Sheets

(56) References Cited

U.S. PATENT DOCUMENTS

| | | | |
|---|---|---|---|
| 5,496,271 A | 3/1996 | Burton et al. | |
| 5,499,994 A | 3/1996 | Tihon et al. | |
| 5,518,504 A | 5/1996 | Polyak | |
| 5,720,415 A | 2/1998 | Morningstar | |
| 5,895,356 A | 4/1999 | Andrus et al. | |
| 6,135,945 A * | 10/2000 | Sultan | 600/30 |
| 6,382,214 B1 | 5/2002 | Raz et al. | |
| 6,460,262 B1 | 10/2002 | Cabak et al. | |
| 6,558,315 B1 | 5/2003 | Kuyava | |
| 6,612,977 B2 | 9/2003 | Staskin et al. | |
| 6,616,653 B2 | 9/2003 | Beyar et al. | |
| 6,652,450 B2 | 11/2003 | Neisz et al. | |
| 6,802,807 B2 | 10/2004 | Anderson et al. | |
| 6,843,766 B1 | 1/2005 | Nemir et al. | |
| 6,896,650 B2 | 5/2005 | Tracey et al. | |
| 6,971,986 B2 | 12/2005 | Staskin et al. | |
| 7,015,253 B2 | 3/2006 | Escandon et al. | |
| 7,048,682 B2 | 5/2006 | Neisz et al. | |
| 7,083,568 B2 | 8/2006 | Neisz et al. | |
| 7,179,219 B2 | 2/2007 | Matlock | |
| 7,267,645 B2 | 9/2007 | Anderson et al. | |
| 7,291,104 B2 | 11/2007 | Neisz et al. | |
| 7,315,762 B2 | 1/2008 | Mosher et al. | |
| 7,996,092 B2 | 8/2011 | Mrva et al. | |
| 8,292,911 B2 | 10/2012 | Brister et al. | |
| 2006/0207601 A1 * | 9/2006 | Nasir | 128/207.14 |
| 2011/0046436 A1 * | 2/2011 | Sokol | 600/30 |
| 2013/0079588 A1 * | 3/2013 | Crabtree et al. | 600/31 |

FOREIGN PATENT DOCUMENTS

| | | |
|---|---|---|
| EP | 0348114 A1 | 12/1989 |
| FR | 2907665 A1 | 5/2008 |
| WO | 0154615 A2 | 8/2001 |
| WO | 2005099618 A2 | 10/2005 |

* cited by examiner

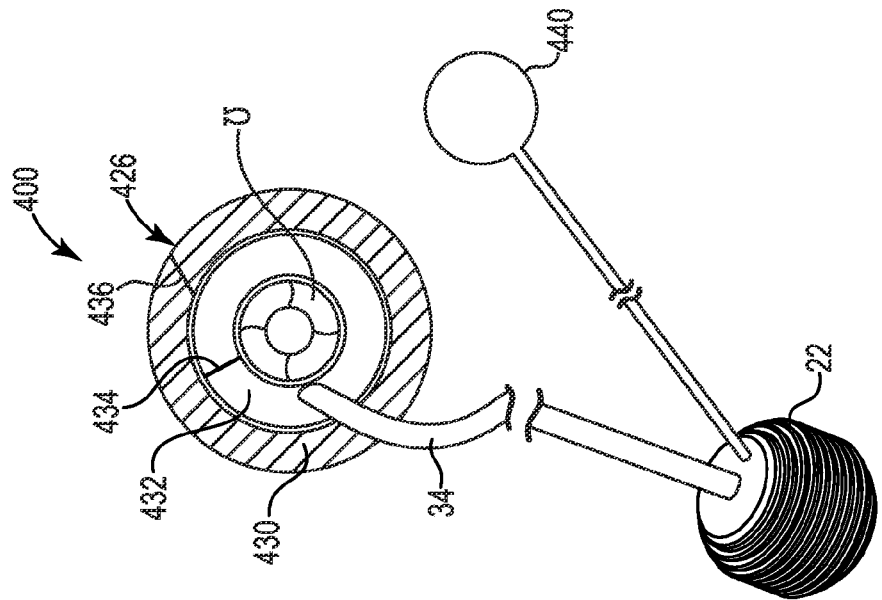
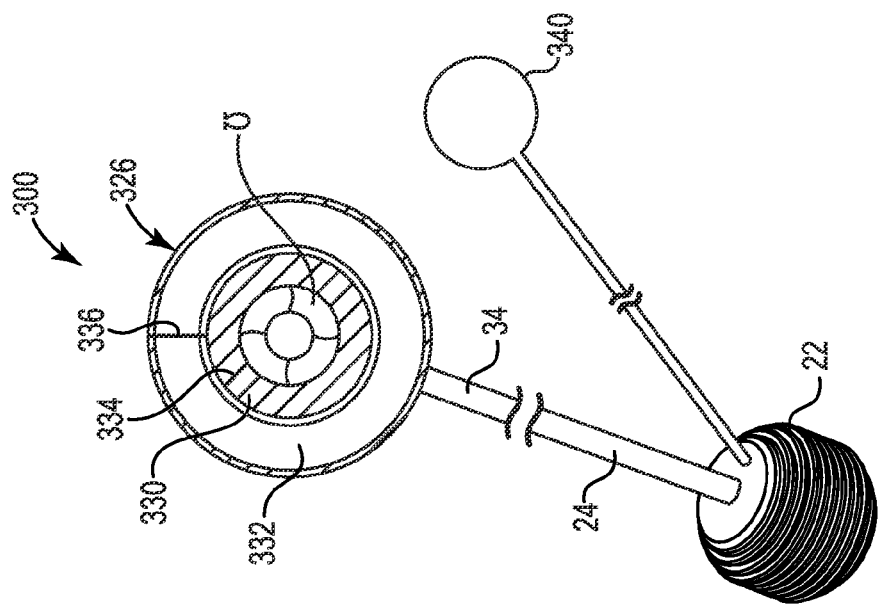

ARTIFICIAL URINARY SPHINCTER HAVING A MULTI-COMPARTMENT CUFF

BACKGROUND

Urinary incontinence affects about 200 million people worldwide and about 25 million people in the US. Urinary incontinence is generally more prevalent in women than in men.

Urinary incontinence in women can be associated with a prolapse of one or more pelvic organs, which can arise from a weakness in the tissues/muscle of the pelvic floor. Urinary incontinence in men can arise after surgical treatment of the prostate glade, which treatment can include removal or weakening of the prostatic sphincter associated with the urinary urethra.

One treatment for urinary incontinence includes placing an artificial sphincter around a portion of the urethra. The artificial sphincter has a closed position that selectively prevents the flow of urine through the urethra, thus providing the user with a comfortable, continent state. The artificial sphincter can be activated to an open position by the user, which opens the urethra and allows the user to selectively pass urine.

Surgeons and patients would welcome advances in the treatment of urinary incontinence.

SUMMARY

One aspect provides an artificial urinary sphincter (AUS) system including a cuff, a pump, and a conduit attachable between the cuff and the pump. The cuff is integrated to include a first compartment and a storage compartment. The first compartment is configured to contact the urethra and the storage compartment communicates with the first compartment. The pump is operable to move the liquid between the first compartment and the storage compartment. The cuff is a pressurizable reservoir that is sized to be placed around a urethra of a user and configured to coapt the urethra in treating urinary incontinence.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 8 is a schematic view of one embodiment of an AUS system showing a cuff in a simplified cross-sectional view.

FIG. 9 is a schematic view of one embodiment of an AUS system showing a cuff in a simplified cross-sectional view.

DETAILED DESCRIPTION

Figure 1:
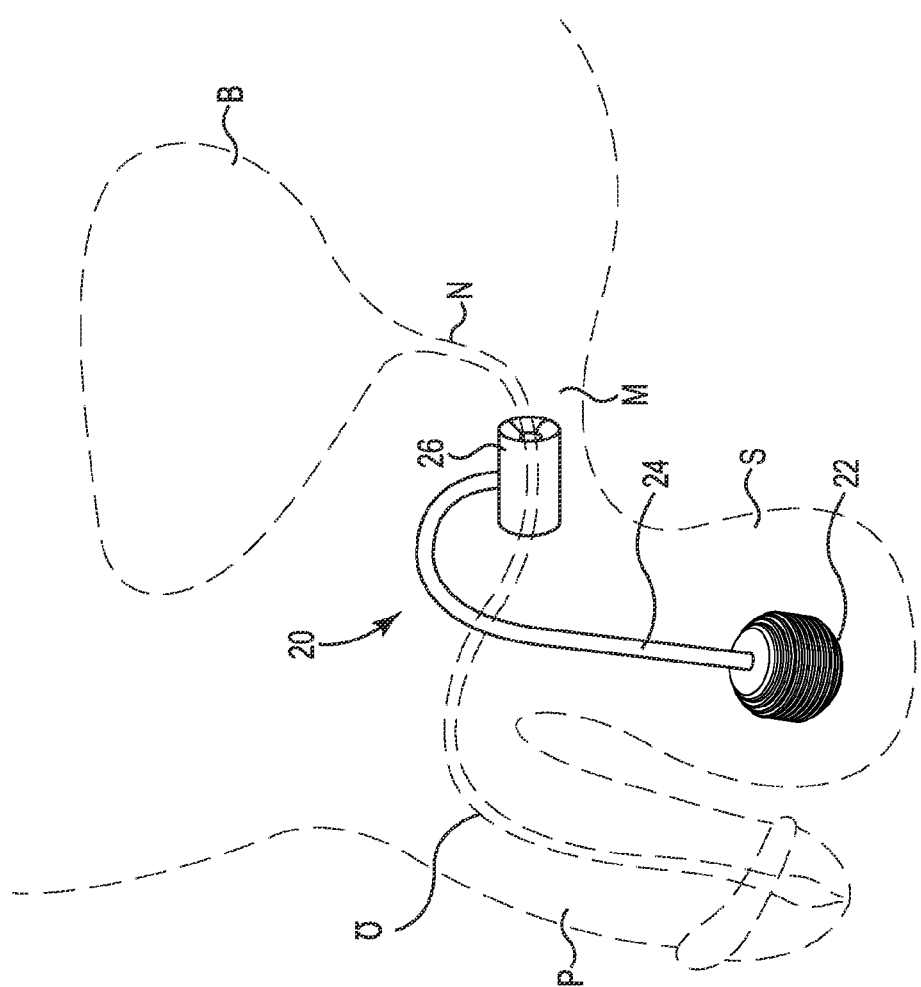
FIG. 1 is a perspective view of one embodiment of an artificial urinary sphincter (AUS) system implanted in the urogenital region of a male patient.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Tissue includes soft tissue, which includes dermal tissue, sub-dermal tissue, ligaments, tendons, or membranes. As employed in this specification, the term "tissue" does not include bone.

As employed in this specification, the term "end" means endmost or the very end point of the subject being described, and the term "end portion" means that segment that is immediately adjacent to the end of the subject being described.

One urinary control system that has found favor with the medical community includes three components cooperatively attached with kink-resistant tubing: an occlusive cuff, a control pump, and a pressure-regulating balloon reservoir. The cuff is implanted around the urethra. The control pump is implanted in the scrotum of a male user. The pressure-regulating balloon reservoir is implanted in the prevesical space, for example through a suprapubic incision followed by dissection of the rectus fascia and a spreading of the linea alba. The three components are filled with liquid (saline) to provide a liquid-filled closed system maintained at an equilibrium pressure that closes the cuff around the urethra. When the user wishes to void, he squeezes and releases the pump several times to move fluid from the cuff into the pressure-regulating balloon reservoir. The cuff "deflates" and opens, which allows the urethra to open and pass urine. The pressure-regulating balloon reservoir, having been pressurized to a pressure above the equilibrium pressure by action of the pump, eventually automatically re-pressurizes the cuff to the equilibrium pressure over the course of several minutes to again inflate the cuff and coapt the urethra.

Embodiments described in this application provide an artificial urinary sphincter (AUS) system that utilizes a series of compartments (or lumens or tubes) having varying durometers. Liquid pumped into the compartment with the lower durometer material will cause the compartment to become firm or stiffer. This action can be harnessed to control the inside diameter of the AUS cuff, which allows the user to control the passage of urine.

Embodiments described in this application provide an artificial urinary sphincter (AUS) system that is provided with a conduit extending between a cuff and a pump of the AUS system. The cuff includes at least two compartments and one of the compartments of the cuff is configured as a storage compartment. The compartments are fabricated from materials having different durometers or hardness and are so configured to have an engineering material response to an equilibrium pressure level that operates coapt the urethra. The different hardness for the material of each compartment allows one compartment to operate as a storage compartment to take up the liquid in the other compartment and store the energy within the cuff of the system.

For example, the storage compartment integrated into the cuff is adapted to store an additional volume of liquid. In one embodiment, the system has a steady state with both of the compartments pressurized and holding liquid, which is usefully employed to coapt the urethra. The liquid in the first compartment is movable into the storage compartment to deflate the first compartment and allow the urethra to pass urine. The storage compartment integrated with the cuff stores the energy of the system for subsequent use in filling (or re-filling) the other compartment in contact with the urethra, which coapts (or re-coapts) the urethra to provide the user with continence. The AUS system described in this patent application is characterized by the absence of a pressure-regulating balloon reservoir that would ordinarily be provided with an artificial urinary sphincter system to store the liquid that inflates the cuff to coapt the urethra.

The AUS system described in this patent application is suited for use both in female patients and in male patients, where the cuff is placed around a portion of the urethra. Female patients will have the pump component implanted in one of the labia or in an abdominal area. Male patients will have the pump component implanted in the scrotum.

One advantage of the two-component AUS system described in this patent application is that the pressure-regulating balloon reservoir is done away with and its function is provided by the storage compartment in the cuff. Thus, fewer components are implanted into the user, which provides a smaller AUS device that is easier to implant and offers a quicker recovery time from the implantation surgery.

FIG. 1 is a perspective view of one embodiment of an artificial urinary sphincter (AUS) system 20 illustrated as implanted in the environment of the male urogenital region. The AUS system 20 includes a pump 22 and a conduit 24 extending from the pump 22 to a cuff 26 that is sized to be placed around a urethra U. The pump 22 is sized for placement within the scrotum S (as one example), and the conduit 24 is attached between the pump 22 and the cuff 26. The AUS system 20 is characterized by the absence of a separate reservoir that is ordinarily provided to retain the liquid that is removed from the urethral cuff to allow the user to pass urine. Embodiments of the AUS system 20 configure the cuff 26 to provide a storage compartment that stores an added volume of liquid to allow a portion of the cuff to shrink/deflate and permit the urethra to open and pass urine.

The AUS system 20 can be referred to as a two component system, where the two components include the pump 22 and the cuff 26. In contrast, a typical three or more component system would include a cuff attached to a reservoir container and a pump attached to the cuff.

The cuff 26 is implanted around the bulbous urethra or around the portion of the urethra descending from the bladder neck N. The cuff 26 is sized to allow placement as close to the bladder B as possible (desired by some surgeons), or positioned distal the bladder neck N as suitably determined by the surgeon. As illustrated in FIG. 1, the cuff 26 is implanted around the urethra U at a location where the urethra U transitions from a vertical orientation communicating with the bladder B to a horizontal orientation extending to the penis P, which corresponds to the area of the urogenital region associated with an increased level of muscle M mass.

The pump 22 is typically implanted within the scrotum S, which provides access to the pump 22 by the user. Other locations for placement of the pump 22 are also acceptable.

The conduit 24 is connected between the cuff 26 and the pump 22, and when implanted thus extends from a location in the scrotum S to a location distal the bladder B. In one embodiment, the conduit 24 is adapted to resist kinking or bending that undesirably might impede the flow of liquid through the conduit 24.

The pump 22 is operable to move liquid within the cuff 26. In one embodiment, the pump 22 includes a pump bulb that communicates with the conduit 24 and operates by providing suction to a portion of the cuff 26 to move the cuff between a configuration that coapts the urethra U and a configuration that allows the urethra U to open to pass urine. One suitable pump is the suction style pump bulb that is illustrated that cooperates with a valve assembly (described below) located within the cuff 26. Other suitable pump mechanisms are also acceptable, including electromechanical pumps, electronic pumps, button-style cavity pumps, and the like. In one embodiment, the pump 22 and the conduit 24 are integrated into a single monolithic unit.

The conduit 24 is generally a thin-walled tube that is attachable between the pump 22 and the cuff 26. In one embodiment, the conduit 24 is separate from the pump 22 and separate from the cuff 26 and connects to these components through a locking mechanism, such as a quick connector or other suitable snap-fit connector.

The system 20, when implanted, provides a closed and pressurized system. The cuff 26 is a pressure reservoir for the system 20. Specifically, the cuff 26 includes multiple compartments and one of the compartments is the pressure reservoir of the system 20.

Figure 2:
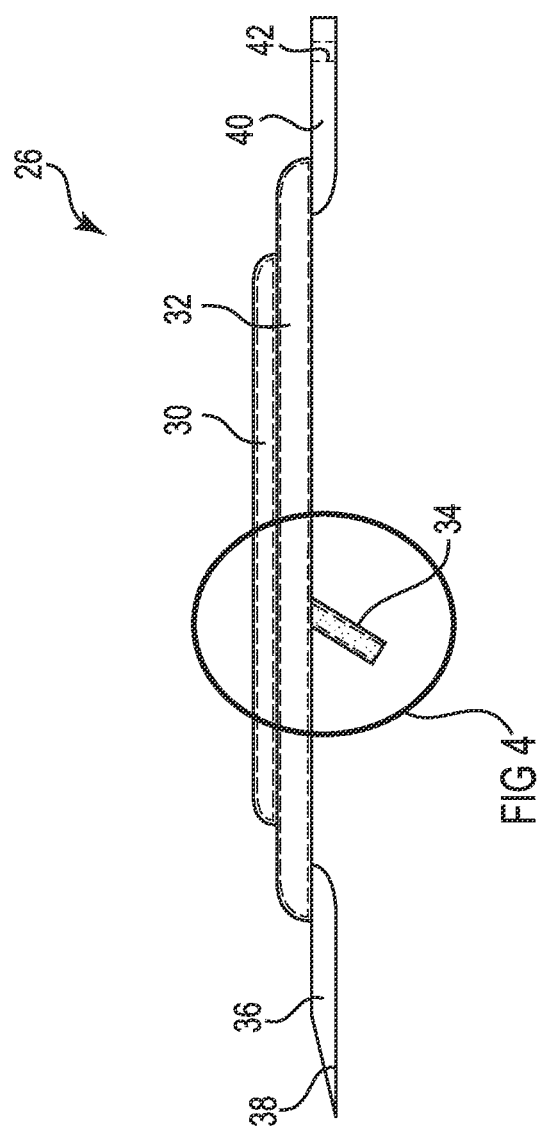
FIG. 2 is a side view of one embodiment of a cuff of the AUS system illustrated in FIG. 1.
Figure 3:
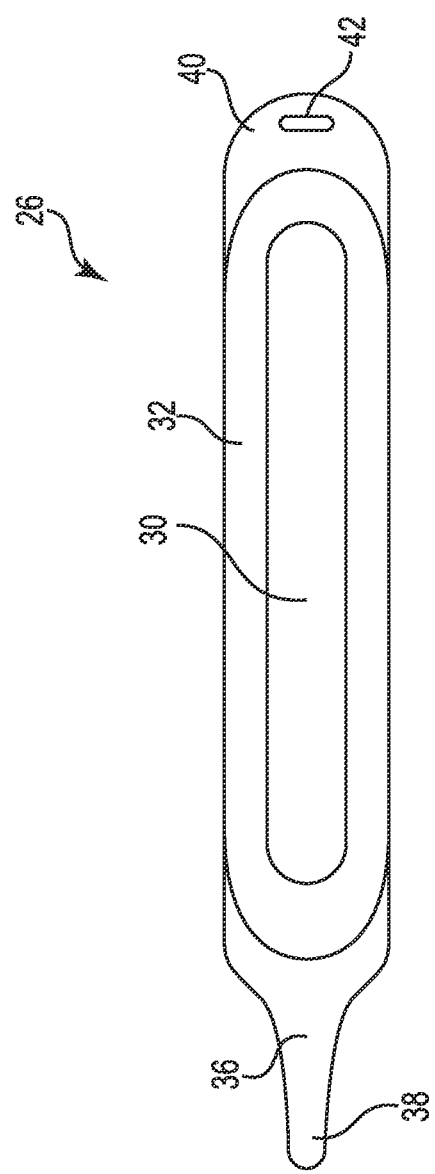
FIG. 3 is a top view of the cuff of the AUS system illustrated in FIG. 2.

FIG. 2 is a side view and FIG. 3 is a top view of one embodiment of the cuff 26. The cuff 26 includes a first compartment 30 in communication with a storage compartment 32 and a connector 34 in communication with the storage compartment 32. The first compartment 30 is configured and sized to be placed in contact with the urethra U. In one embodiment, the storage compartment 32 is flexible and expandable and communicates with the first compartment 30. For example, the storage compartment 32 is sized to receive the liquid that is retained in the first compartment 30 as the first compartment 30 is deflated. When the user desires to pass urine, liquid is moved from the first compartment 30 into the storage compartment 32, which results in an opening of the urethra that allows the user to pass urine.

The cuff 26 is placed around a portion of the urethra, for example during surgery. In one embodiment, the cuff 26 includes an optional first end portion 36 that provides a tab 38 and an optional second end portion 40 that is formed to include a slot 42. Insertion of the tab 38 and the slot 42 forms the cuff and a substantially circular shape suited for placement around the urethra. Alternatively, the opposing ends of the cuff 26 may be sutured into position around the urethra of the user. The first compartment 30 is sized to contact most of the perimeter of the urethra, or the entire perimeter of the urethra, and this sizing is generally selected by the surgeon. The cuff 26 is generally about 2 cm wide and have varying lengths suited to different anatomical sizes, where the lengths are provided in a range between 4-11 cm.

In one embodiment, the first compartment 30 and a storage compartment 32 are integrated into a single monolithic unit. It is desirable that the extension properties of the storage compartment 32 are different from the extension properties of the first compartment 30. Specifically, it is desirable to provide the storage compartment 32 with the level of expandability and/or extends ability that allows the storage compartment 32 to uptake liquid from the first compartment 30. In one embodiment, the first compartment 30 is formed from a material having a first durometer (having units of Shore-A) and the storage compartment 32 is formed from a material having a second durometer that is different than the first durometer. In one embodiment, it is desirable that the first compartment 30 is soft and suitable for contact with the urethra, and that the storage compartment 32 is more extensible than the first compartment 30. One suitable range hardness for the first compartment 30 is provided by a material having a Shore-A durometer of in a range of 50-70 Shore-A. One suitable range of hardness for the storage compartment 32 is provided by a material having a Shore-A durometer in a range of 10-49 Shore-A. Suitable material for fabricating the compartments 30, 32 includes silicone elastomer selected to have the appropriate value of Shore-A hardness discussed above.

Figure 4:
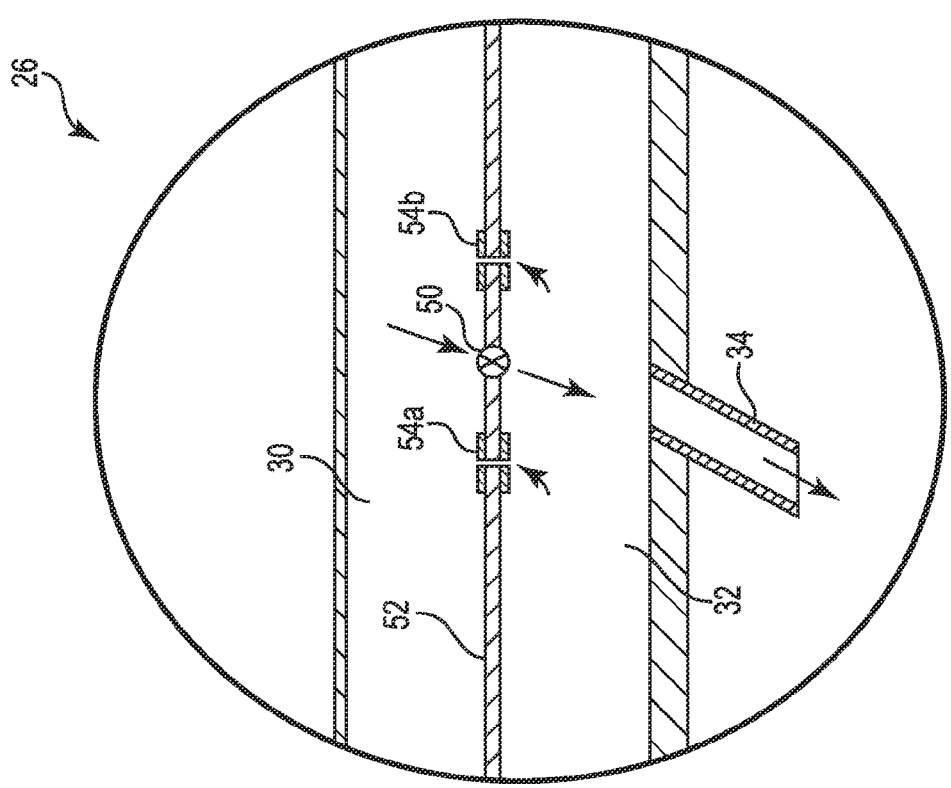
FIG. 4 is a cross-sectional view of a portion of the cuff illustrated in FIG. 2.

FIG. 4 is a cross-sectional view of a portion of the cuff 26. The first compartment 30 is in communication with the storage compartment 32 by a valve assembly 50 located in an interface wall 52. In one embodiment, the valve assembly 50 is provided as a one-way valve that allows liquid to exit the first compartment 30 and enter the storage compartment 32. Suitable valve assemblies 50 include a ball valve or a poppet valve or other such valves.

During use, liquid is stored in the first compartment 30 to provide the first compartment 30 with the firmness that is configured to coapt the urethra U. When the user desires to pass urine, the user operates the pump 22 (FIG. 1). The pump 22 communicates with the storage compartment 32 through connection with the connector 34. The storage compartment 32 communicates with the first compartment 30 through the valve assembly 50. Manipulation of the pump 22 draws liquid from the first compartment 30 across the valve assembly 50 and into the storage compartment 32. In one embodiment, the actuation of the pump 22 creates a suction that draws liquid from the first compartment 30 across the valve assembly 50 and into the storage compartment 32. In one embodiment, manipulation of the pump 22 causes the pressure in the storage compartment 32 to increase, which results in the storage compartment 32 expanding away from the interface wall 52.

The transfer of the liquid from the first compartment 30 into the storage compartment 32 (for example by pumping the pump 22) results in a reduction in the firmness and the first compartment 30 that removes pressure that was applied against the urethra U. In this configuration, the urethra U is permitted open and pass urine.

It is desirable to return the user to a comfortable, continent state soon after the user passes urine. In one embodiment, the interface wall 52 includes one or more bleeder valves 54a, 54b configured to allow the liquid stored in the storage compartment 32 to slowly flow back into the first compartment 30. In one embodiment, the bleeder valve 54 is provided as an orifice formed in a diaphragm, although other forms of bleeder valve are also acceptable. In any regard, the liquid in the storage compartment 32 (that is stored at a pressure above the equilibrium pressure of the system 20) has a pathway provided by the bleeder valve 54 that allows the system 20 to return to equilibrium. In the equilibrium state the liquid returns to the first compartment 30 and the user is returned to a continent state.

Figure 5B:
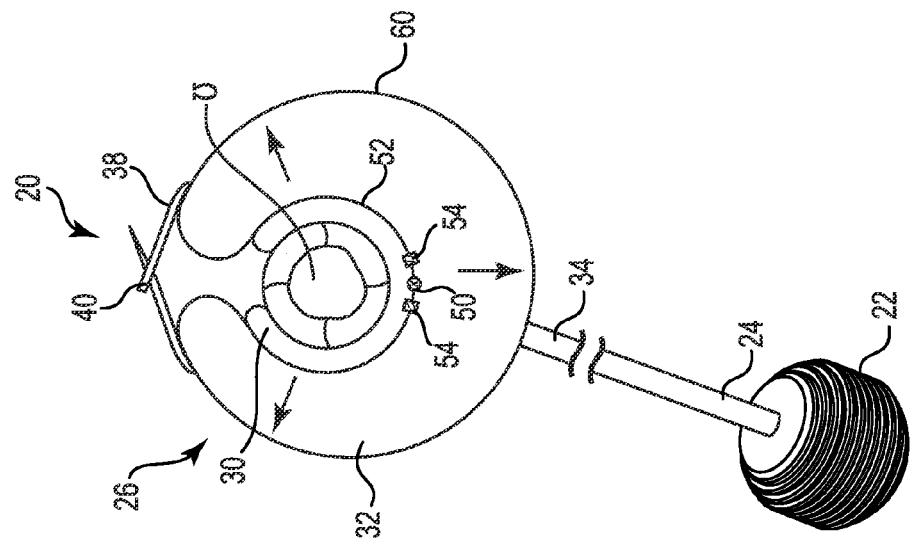
FIG. 5B is a side schematic view of one embodiment of the system illustrated in FIG. 1 in an activated state allowing the urethra to pass urine.
Figure 5A:
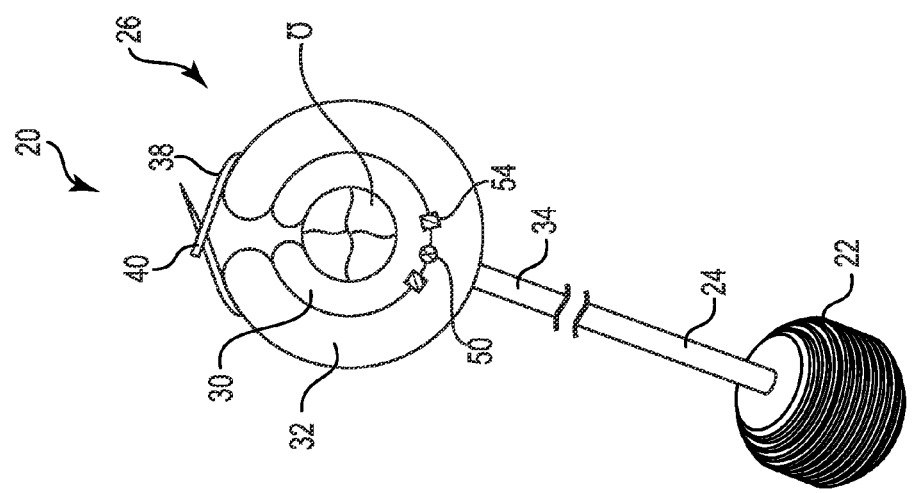
FIG. 5A is a side schematic view of one embodiment of the system illustrated in FIG. 1 in an equilibrium state configured to coapt a urethra of a user.

FIG. 5A is a side schematic view of the system 20. The cuff 26 is wrapped around a portion of the urethra U and secured in position by coupling the tab 38 with the end portion 40. The system 20 is an equilibrium state with the first compartment 30 and the storage compartment 32 maintained at the same equilibrium pressure. The first compartment 30 is maintained at the equilibrium pressure, which is configured to apply a selected pressure against the urethra U that is sufficient to coapt the urethra U. The system 20 provides a first interior cuff in the first compartment 30 that is adapted to contact the urethra U and a second cuff exterior to the interior cuff in the storage compartment 32.

FIG. 5B is a side schematic view of the system 20 in an activated state allowing the urethra to pass urine. The pump 22 has been manipulated to draw liquid out of the first compartment 30, through the valve assembly 50, and into the storage compartment 32. An increase in pressure in the storage compartment 32 causes the storage compartment 32 to expand or extend away from the interface wall 52. The first compartment 30 is deflated or flaccid since liquid has been removed from the first compartment 30. The exposed exterior wall 60 of the storage compartment 32 is more expandable than the interface wall 52, which allows the storage compartment 32 to swell in response to the transfer of liquid from the first compartment 30 into the storage compartment 32. As illustrated, the first compartment 30 is deflated and the urethra U is opened to allow urine to pass.

The bleeder valve 54 is configured to allow the pressurized liquid in the storage compartment 32 to be subsequently transferred across the interface wall 52 and back into the first compartment 30, which returns the system 22 to its equilibrium pressure.

The system 20 is designed to provide a closed system with an equilibrium pressure Pe selected to provide a sufficient pressure to coapt the urethra when the AUS system 20 is in the rest state, which ensures that the user is maintained in a comfortable and continent state until s/he desires to void urine. A suitable range for equilibrium pressures Pe of the closed AUS system 20 is between about 30-80 cm of water. One suitable equilibrium pressure Pe for the AUS system 20 is about 60 cm of water. The storage compartment 32 is configured to expand at a storage pressure Ps that is greater than the equilibrium pressure Pe as the first compartment 30 is deflated. A suitable range for storage pressures Ps of the AUS system 20 is between about 85-120 cm of water. One suitable storage pressure Ps for the AUS system 20 is about 90 cm of water.

The system 20 includes the cuff 26 that is a pressure-regulating liquid storage reservoir 26. At least a portion of the pressure-regulating liquid storage reservoir 26 is pressurizeable to a pressure above the steady-state equilibrium pressure of the system. The pressure-regulating liquid storage reservoir 26 includes the storage compartment 32 that inflates to hold the volume of liquid moved from the first compartment 30, and after holding the increased pressure allows the system 20 to regulate back to the equilibrium pressure by allowing liquid to flow through the bleeder valves 54. The pressure-regulating liquid storage reservoir 26 is sized to be placed around a urethra of a user and is configured to coapt the urethra in treating urinary incontinence.

In contrast to other AUS systems that have a cuff and a pressure-regulating balloon, the system 20 includes a cuff 26 that plays the role of a pressure-regulating balloon by holding the volume of liquid that acted to coapt the urethra (the liquid in the first compartment), and the pressure-regulating liquid storage reservoir 26 plays the role of the cuff in that it is sized to be placed around a urethra of a user.

Other embodiments of AUS systems providing compartments having varying durometers are described below.

Figure 6B:
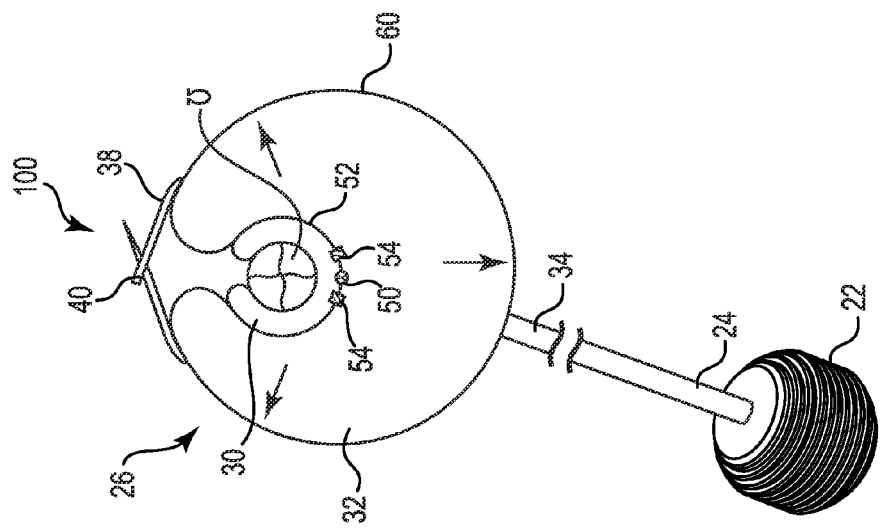
FIG. 6B is a side schematic view of the system illustrated in FIG. 6A in an activated state that closes the urethra.
Figure 6A:
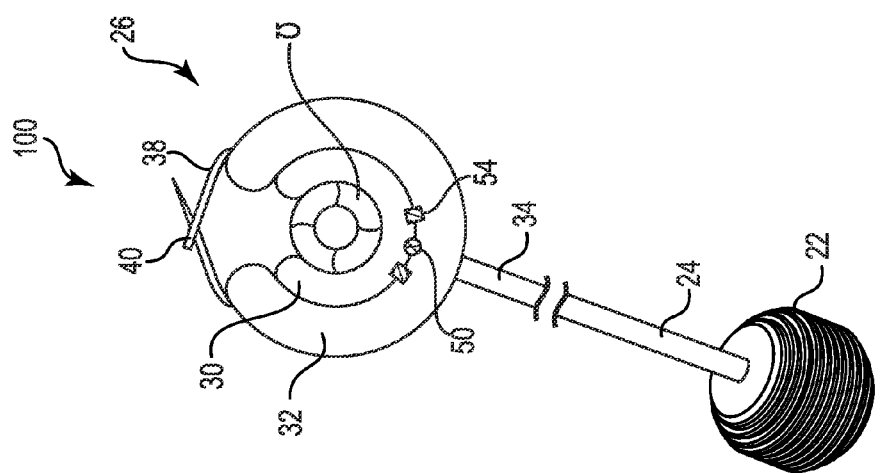
FIG. 6A is a side schematic view of one embodiment of an AUS system in an open configuration allowing the user to pass urine.

FIG. 6A is a side schematic view of one embodiment of an artificial urinary sphincter (AUS) system 100 in an open configuration allowing the user to pass urine. FIG. 6B is a side schematic view of the system 100 in an activated state that closes the urethra. The system 100 is similar to the system 20 described above but the system 100 is provided with a steady state in which the urethra U is maintained in an open configuration for the passage of urine. The user, to achieve a continent state, operates the pump 22 to move liquid out of the first compartment 30 and into the storage compartment 32. Thus, the system 100 will default to an open urethra condition if a leak develops over a period of time and use.

In one embodiment, the material hardness for the first compartment 30 is selected to be stiff to provide the urethra with an open configuration (FIG. 6A) when the cuff 26 is in the steady state and pressurized at an equilibrium pressure Pe of about 60 cm of water. Deflating the first compartment 30 and pressurizing the storage compartment 32 to a storage pressure of about 90 cm of water is adapted to close the urethra to provide the user with a continent state (FIG. 6B).

Figure 7B:
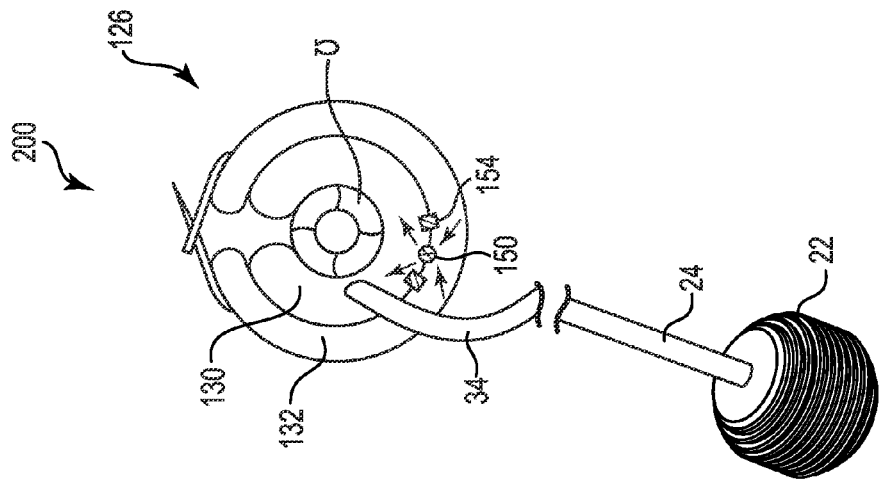
FIG. 7B is a side schematic view of the system illustrated in FIG. 7A in an activated state that opens the urethra.
Figure 7A:
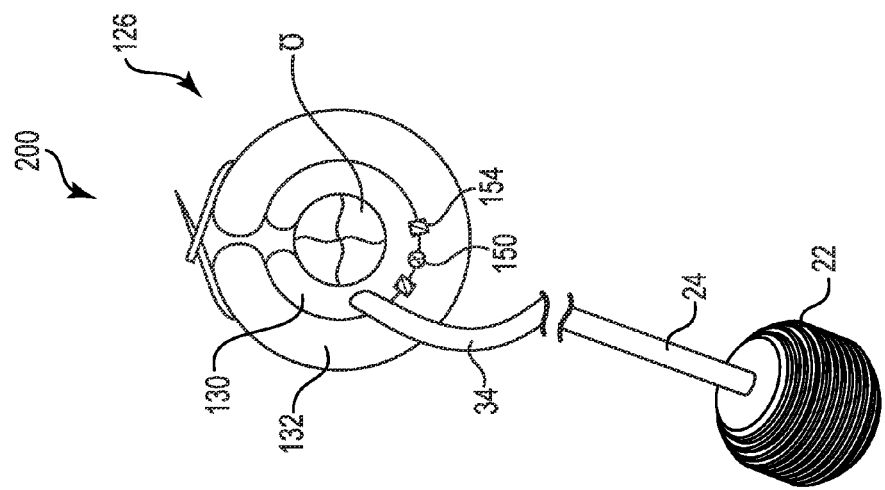
FIG. 7A is a side schematic view of one embodiment of an AUS system in a closed state that prevents the flow of urine through the urethra.

FIG. 7A is a side schematic view of one embodiment of an artificial urinary sphincter (AUS) system 200 in a closed state that prevents the flow of urine through the urethra. FIG. 7B is a side schematic view of the system 200 in an activated state that opens the urethra.

The system 200 includes the pump 22 attached to the conduit 24 that is attached to an inner annulus 130 of a multi-annulus cuff 126.

In one embodiment, the cuff 126 is provided with an inner annulus 130 and an outer annulus 132, where the inner annulus 130 is configured as a storage compartment for the cuff 126. The conduit 124 is in fluid communication with the inner annulus 130. A fluid transfer valve 150 is provided between the first annulus 130 and a second annulus 132. In one embodiment, the fluid transfer valve 150 is provided as a one-way valve that allows liquid to flow from the second annulus 132 into the first annulus 130, which inflates the first annulus 130 (or the storage annulus 130).

In one embodiment, one or more bleeder valves 154 is/are located at an interface between a first annulus 130 and a second annulus 132. The bleeder valve 154 is provided to allow the additional liquid stored in the first annulus 130 (or the storage annulus 130) to eventually flow and transfer back into the second annulus 132.

In the embodiment illustrated in FIGS. 7A and 7B, the first annulus 130 is provided with a softer material (or a lower durometer material) as compared to the second annulus 132. The outer, or second annulus 132 is configured to constrict in the steady state and close the urethra U. The softer material of the first annulus 130 is configured to expand when the liquid is transferred from the second annulus 132 and into the first annulus 130. In this configuration, the inside diameter of the first annulus 130 is equal to or larger than the outside diameter of the urethra U when urethra is open for the passage of urine.

FIG. 8 is a schematic view of one embodiment of an AUS system 300 showing a cuff 326 in a simplified cross-sectional view as placed around the urethra U. The cuff 326 includes a solid and non-inflatable annulus 330 of material integrated with an inflatable compartment 332. The solid and non-inflatable annulus 330 of material is wrapped around the urethra and secured at a parting line 334. The inflatable compartment 332 is wrapped around the non-inflatable annulus 330 and is secured at a parting line 336, for example by a suture or by adhesive. The pump 22 communicates with the inflatable compartment 332 by the conduit 24 that is connected to the connector 34. The non-inflatable annulus 330 of material contacts the urethra U and is configured to reduce tissue erosion of the urethra U. In one embodiment, the non-inflatable annulus 330 of material is provided as an o-ring of soft polymer and is collapsible when the inflatable compartment 332 is pressurized or inflated by the pump 22. The cuff 326 is characterized by an absence of internal valves employed to harness the inflation liquid, and the inflation volume of liquid is stored in a reservoir 340.

FIG. 9 is a schematic view of one embodiment of an AUS system 400 showing a cuff 426 in a simplified cross-sectional view as placed around the urethra U. The cuff 426 includes a solid and non-inflatable annulus 430 of material integrated with an inflatable compartment 432. The inflatable compartment 432 is wrapped around the urethra and secured at a parting line 434. The solid and non-inflatable annulus 430 of material is wrapped around the inflatable compartment 432 and is secured at a parting line 436, for example by a suture or by adhesive. The pump 22 communicates with the inflatable compartment 432 by the conduit 24 that is connected to the connector 34. The inflatable compartment 432 contacts the urethra U and is configured to coapt the urethra when inflated. The solid and non-inflatable annulus 430 of material provides a "backboard" of material against which the inflatable compartment 432 pushes, which allows the inflatable compartment 432 to effectively coapt the urethra U at a lower inflation pressure (for example, at an inflation pressure of 20-30 cm of water). In one embodiment, the non-inflatable annulus 430 of material is provided as a solid o-ring of polymer material, such as silicone or urethane or a polyolefin such as polyethylene or polypropylene. The cuff 426 is characterized by an absence of internal valves and the like, however the inflation volume of liquid is stored in a reservoir 440.

A method of treating a patient suffering from urinary incontinence includes a surgical procedure to implant any one of the systems described above. The patient is prepared for surgery in a manner prescribed by the hospital or clinic as supervised and approved by the surgeon. The perineal area of the patient is cleaned with suitable cleansers and prepared for surgery. A perineal incision is made on the midline of the patient, and tissue is dissected to expose the bulbospongiosus muscle supporting the urethra U. The surgeon will dissect laterally to free the fascia around the bulbospongiosus muscle and expose a portion of the length of the urethra U. The bulbospongiosus muscle is immobilized, for example by clamping laterally to each side of the patient, which exposes the urethra. The surgeon dissects additional tissue and muscle by "tunneling" around the posterior side of the urethra to create a pathway around a circumference of the urethra. The cuff 26 is traversed along the pathway around the urethra U until a portion of the cuff 26 is posterior to the urethra U with the tab 36 and a slot 42 of the cuff 26 anterior to the urethra U. The tab 36 is inserted into the slot 42 to secure the cuff 26 around the urethra U. in other embodiment, the cuff is directed around the urethra and suitable sutured or otherwise secured in position.

The surgeon typically confirms performance of the implanted cuff by injecting liquid into the connector 34. The tube 26 and the pump 22 are attached to the cuff 26. For example, the pump 22 is located in the scrotum (male) or labia (female) of the user and the tube 26 is connected between the pump and the cuff 26 that has been placed around the urethra U. The surgeon will pressurize the system 20 and equilibrium pressure Pe and cause the cuff 26 to coapt the urethra U. The surgeon will confirm that operation of the pump 22 will move liquid into or from the cuff 26, depending upon the embodiment, thus opening the urethra U and allowing the patient to pass urine. The surgical site is closed after confirmation of performance of the system 20.

Embodiments of methods of treating a patient suffering from urinary incontinence with the system 20 include providing an implantable device to treat urinary incontinence, the device including a pressure-regulating liquid storage reservoir, a pump, and a conduit attachable between the pressure-regulating liquid storage reservoir and the pump; and implanting the pressure-regulating liquid storage reservoir around at least a portion of a urethra of a user.

Embodiments of methods of treating a patient suffering from urinary incontinence with the system 20 include creating a perineal incision in a patient; and inserting a pressure-regulating liquid storage reservoir through the perineal incision and implanting the pressure-regulating liquid storage reservoir around at least a portion of a urethra of a user.

Embodiments of the artificial urinary sphincter (AUS) system described above include a fully functional system for treating urinary incontinence that operates in the absence of a reservoir provided separate from the tubing, cuff, and pump. The tube or tubing is connected between the cuff and the pump and includes a lumen that is configured to expand to provide the lumen/system with an inflatable storage compartment.

Although specific embodiments have been illustrated and described in this patent application, it will be appreciated by those of ordinary skill in the art that a variety of alternate and/or equivalent implementations may be substituted for the specific embodiments shown and described without departing from the scope of the invention. This patent application is intended to cover any adaptations or variations of medical devices, as discussed above. Therefore, it is intended that this invention be limited only by the claims and their equivalents.

What is claimed is:

1. An artificial urinary sphincter system comprising:
a pressure-regulating liquid storage reservoir that is sized to be placed around a urethra of a user and is configured to coapt the urethra in treating urinary incontinence, the pressurizable reservoir comprising a first compartment and a storage compartment, the first compartment configured to be positioned about the urethra and being coaxially received by the storage compartment such that the first compartment and the storage compartment are separated by an interface wall, the interface wall including a valve configured to permit fluid communication between the first compartment and the storage compartment;
a pump; and
a conduit attachable between the pressure-regulating liquid storage reservoir and the pump.

2. The system of claim 1, wherein the pump is operable to cause a liquid to move between the first compartment and the storage compartment.

3. A method of treating urinary incontinence, the method comprising:
providing an implantable device to treat urinary incontinence, the device including:
a pressure-regulating liquid storage reservoir, the pressure-regulating liquid storage reservoir comprising a first compartment and a storage compartment, the first compartment configured to be positioned about the urethra and being coaxially received by the storage compartment such that the first compartment and the storage compartment are separated by an interface wall, the interface wall including a valve configured to permit fluid communication between the first compartment and the storage compartment,
a pump, and
a conduit attachable between the pressure-regulating liquid storage reservoir and the pump;
implanting the pressure-regulating liquid storage reservoir around at least a portion of a urethra of a user;
implanting the pump into one of a scrotum of a male user and a labia of a female user; and
connecting the conduit to the pressure-regulating liquid storage reservoir and to the pump.

* * * * *